United States Patent
Schmidt

(10) Patent No.: US 10,098,597 B2
(45) Date of Patent: Oct. 16, 2018

(54) MOTORIZED MEDICAL DEVICE AND METHOD FOR OPERATING SUCH A DEVICE

(71) Applicant: Verena Schmidt, Erbendorf (DE)

(72) Inventor: Verena Schmidt, Erbendorf (DE)

(73) Assignee: Siemens Aktiengesellschaft, München (DE)

( * ) Notice: Subject to any disclaimer, the term of this patent is extended or adjusted under 35 U.S.C. 154(b) by 160 days.

(21) Appl. No.: 15/047,854

(22) Filed: Feb. 19, 2016

(65) Prior Publication Data
US 2016/0242715 A1    Aug. 25, 2016

(30) Foreign Application Priority Data

Feb. 24, 2015 (DE) .......................... 10 2015 203 311

(51) Int. Cl.
*H05G 1/64* (2006.01)
*A61B 6/00* (2006.01)

(52) U.S. Cl.
CPC ............ *A61B 6/4405* (2013.01); *A61B 6/461* (2013.01); *A61B 6/54* (2013.01); *A61B 6/4441* (2013.01)

(58) Field of Classification Search
CPC ......... A61B 6/00; A61B 6/4405; A61B 6/461; A61B 6/54; A61B 6/10; A61B 6/102
USPC ........ 378/98, 98.2, 98.5, 117, 198, 204, 207
See application file for complete search history.

(56) References Cited

U.S. PATENT DOCUMENTS

| 9,766,072 | B2 * | 9/2017 | Kim ................... B62D 15/0295 |
| 2004/0000630 | A1 | 1/2004 | Spartiotis et al. |
| 2010/0284601 | A1 | 11/2010 | Rubner et al. |
| 2010/0299014 | A1 | 11/2010 | Bouvier |
| 2011/0170662 | A1 | 7/2011 | Baumgart |
| 2011/0170668 | A1 | 7/2011 | Ozawa et al. |
| 2013/0243160 | A1 | 9/2013 | Graumann et al. |
| 2013/0253485 | A1 | 9/2013 | Fehre et al. |
| 2014/0372037 | A1 | 12/2014 | Kim |

FOREIGN PATENT DOCUMENTS

| CN | 1535387 A | 10/2004 |
| CN | 101542240 A | 9/2009 |
| CN | 102232836 A | 11/2011 |
| CN | 102475549 A | 5/2012 |
| DE | 102011082680 A1 | 3/2013 |
| DE | 102012204018 A1 | 9/2013 |

OTHER PUBLICATIONS

German Office Action for related German Application No. 10 2015 203 311.2, dated Jan. 22, 2016, with English Translation.
Chinese Office Action for Chinese Patent Application No. 201610100495.4, dated Apr. 18, 2018.

* cited by examiner

*Primary Examiner* — Jurie Yun
(74) *Attorney, Agent, or Firm* — Lempia Summerfield Katz LLC

(57) ABSTRACT

A mobile medical device drivable on rollers or wheels on the floor by way of a motor is provided, wherein the medical device is configured to take a planned route. The device has an optical display apparatus embodied to optically display at least one future movement feature of the medical device on the planned route. A visualization of the route planning helps the user to better estimate the future movement behavior of a medical device.

20 Claims, 2 Drawing Sheets

MOTORIZED MEDICAL DEVICE AND METHOD FOR OPERATING SUCH A DEVICE

This application claims the benefit of DE 10 2015 203 311.2, filed on Feb. 24, 2015, which is hereby incorporated by reference in its entirety.

TECHNICAL FIELD

The embodiments relate to a mobile medical device drivable on wheels on the floor by way of a motor, the medical device being embodied to take a planned route, and an associated method for operating a medical device drivable by way of a motor. By way of example, such medical devices are mobile x-ray devices or else mobile patient displacement apparatuses on wheels.

BACKGROUND

A mobile C-arm x-ray device, which may drive in all directions on wheels or rollers on the floor of a room, is an example of a medical device drivable by way of a motor. The device is driven to an operating table in order to record x-ray images of the treatment region at the patient prior to, during, and after a surgical intervention. In order to obtain clear access to the work region at the operating table, the mobile C-arm x-ray device may be driven back into a park position away from the operating table after each recording or each recording cycle. Application DE 10 2012 204 018 A1 describes such a mobile C-arm x-ray device.

Such C-arm x-ray devices may be displaced autonomously (e.g., it is not accompanied by the operator during a drive) or semi-autonomously (e.g., it is accompanied by the operator during a drive) with motor-driven assistance. In the case of autonomously or semi-autonomously displaceable medical devices that allow free trajectory planning (=route planning) for reaching an end position from a start position, a user may not identify the route that the medical device will select. The medical staff may be unsettled thereby and may not react appropriately to the driving medical device in certain circumstances.

SUMMARY AND DESCRIPTION

The scope of the present invention is defined solely by the appended claims and is not affected to any degree by the statements within this summary. The present embodiments may obviate one or more of the drawbacks or limitations in the related art.

It is an object of the embodiments to specify a medical device drivable by way of a motor and a method for operating such a medical device, which improve route planning or trajectory planning of the medical device.

The object addressed is achieved by the mobile medical device drivable by way of a motor and the method for operating a mobile medical device drivable by way of a motor.

The mobile medical device drivable on the floor by way of a motor has a device, with the aid of which the short-term and/or medium-term planned trajectory or planned route is visualized to the operating staff. By way of example, this is brought about by luminous segments arranged at the medical device. By a luminous display made of a plurality of segments, it is possible to indicate to the operating staff the direction in which the medical device is driving in the short term (e.g., in three seconds) and in the medium term (e.g., in ten seconds). Thus, the operating staff may identify in good time which route the medical device will take according to plan and whether the medical device, e.g., will drive around an object and by which route. By way of example, medical devices may be drivable x-ray devices or drivable patient couches.

Movement features are features of a spatial driving movement of an object, such as, e.g., the direction of travel or the driving speed.

In certain embodiments, a mobile medical device drivable on rollers or wheels by way of a motor is provided, the medical device being embodied to take a planned route, wherein the medical device has an optical display apparatus embodied to optically display at least one future movement feature of the medical device on the planned route.

A visualization of movement features of the planned route helps the user to better estimate the future movement behavior of the medical device. The medical device is not displaced in the room without knowledge of the future route; instead, the user identifies the trajectory planning for a predeterminable period of time in advance. The visualization by way of the optical display apparatus allows the user to identify risks at an early stage and the user may thus react appropriately. In the case of semiautonomous systems, the user may then for example override the clearance to travel where necessary (e.g., risk of collision).

In certain embodiments, the movement feature may be a direction of travel and/or a driving speed of the medical device.

In a further embodiment, the optical display apparatus may be embodied to display at least one first movement feature occurring after a first period of time and at least one second movement feature occurring after a second period of time. As a result, a short-term and medium-term preview is possible.

In a further embodiment, the first and the second movement feature may be distinguished by different colors.

In a further embodiment, the first period of time may lie between one and three seconds and the second period of time may lie between three and ten seconds, which may be suitable values for a short-term and medium-term route preview, respectively.

In a further embodiment, the optical display apparatus may have luminous segments, wherein the direction of travel is displayable by the spatial arrangement of the luminous segments.

In a further refinement, the drivable medical device has a control unit embodied to take into account the current driving speed of the medical device for determining the first and second period of time. As a result, the preview of the speed of the driving medical device may be adapted. In the case of a high speed, the outlook may be further into the future.

In certain embodiments, a method is provided for operating a mobile medical device drivable on rollers or wheels by way of a motor, with planning of a future route, wherein at least one future movement feature of the medical device on the planned route along the floor is optically displayed by an optical display apparatus of the medical device.

The method is carried out using a medical device drivable by way of a motor.

BRIEF DESCRIPTION OF THE DRAWINGS

Further peculiarities and advantages will become clear from the following explanations of a plurality of exemplary embodiments on the basis of schematic drawings.

DETAILED DESCRIPTION

Figure 1:
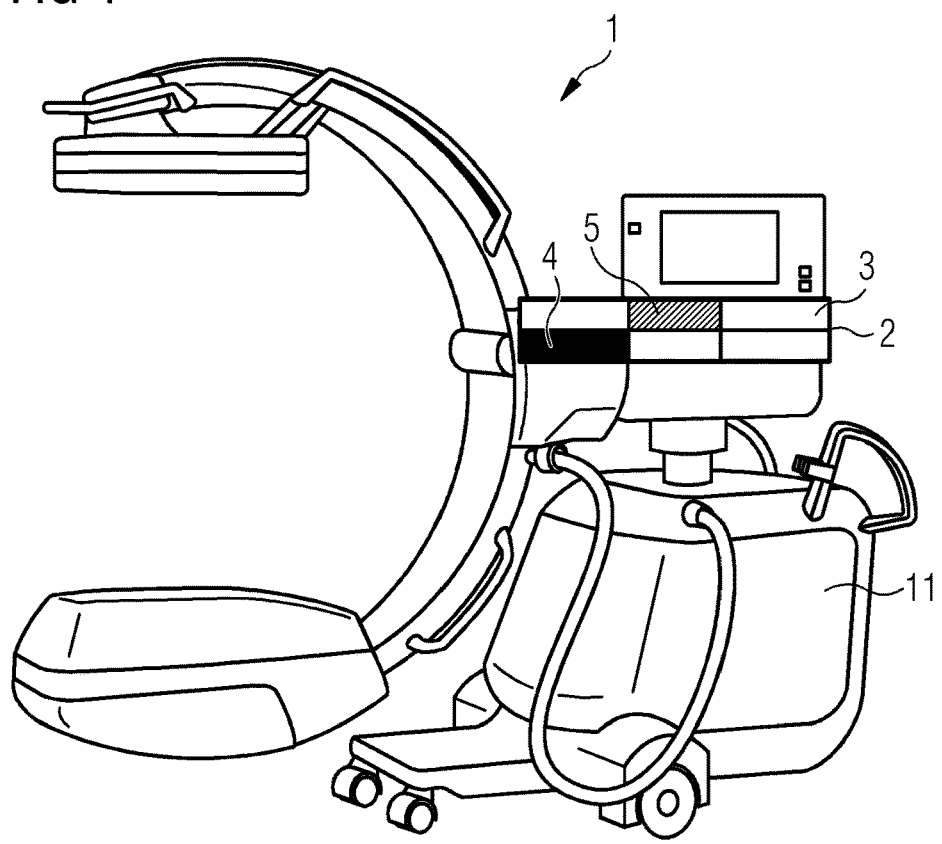
FIG. 1 depicts an example of a mobile C-arm x-ray device with an optical display apparatus.

FIG. 1 depicts a mobile C-arm x-ray device 1 on wheels as an example of a mobile medical device drivable by way of a motor. For the purposes of displaying route planning or trajectory planning, the mobile C-arm x-ray device 1 has an optical display apparatus 2, easily visible for users, displaying to the users movement features of the short-term (=first period of time) and the medium-term (=second period of time) route guidance by a plurality of luminous segments 3. With the aid of the display apparatus 2, both the user and other persons are able to identify the path that the C-arm x-ray device 1 will, according to plan, take in future on the floor in the room.

To this end, the optical display apparatus 2 has, e.g., six luminous segments 3, which are arranged above one another in two rows. The lower three luminous segments 3 specify the first direction of travel 4 at a future time after the first period of time as a first movement feature. By way of example, the first period of time has a length of three seconds and therefore specifies a time three seconds into the future. The left-hand luminous segment 3, 4 of the lower row is active (e.g., the segment is luminous or blinks) and therefore specifies the planned first direction of travel after three seconds.

In FIG. 1, the left-hand luminous segments 3 symbolize travel (=movement) to the left, the right-hand luminous segments 3 symbolize travel to the right and the central luminous segments 3 symbolize travel straight ahead. Since the left-hand lower luminous segment 3, 4 is luminous, the C-arm x-ray device travels, or turns, to the left three seconds after the current position.

The upper luminous segments 3 specify the second direction of travel 5 at a time after the second period of time. By way of example, the second period of time is ten seconds long. The central luminous segment 3, 5 of the upper row is active (e.g., the segment is luminous or blinks) and therefore specifies the planned second direction of travel after ten seconds. Since the central luminous segment 3, 5 of the upper row is luminous, the C-arm x-ray device 1 travels straight ahead after ten seconds calculated from the current moment.

The optical display apparatus 2 is controlled with the aid of the control unit 11. In the process, it is also possible to take into account the current driving speed of the C-arm x-ray device 1 for the purposes of determining the first and second period of time. By way of example, the outlook may be further into the future in the case where the C-arm x-ray device is traveling quickly. The first and the second period of time are selected to be longer. The planned routes are also stored in the control unit 11.

By way of example, the planned speed after the first and second period of time is a different movement feature. This may also be visualized, alternatively or additionally, with the aid of the optical display unit 2. By way of example, the blinking frequency may represent the speed.

The optical display apparatus may have an optical display, a luminous display, a signaling lamp, an optical direction display, or an optical route display.

An algorithm may be implemented in the control unit 11 in the case of travel along a path full of bends, which algorithm correspondingly adapts the periods of time more often in the case of frequent changes of direction.

Depending on the application, the system may also have only one display for the movement features or else have more than 2 stages.

Use may also be made of only a single segment display that, however, has the option of visualizing the short-term and medium-term route to the user in the case of changes in the direction by color transitions.

Figure 2:
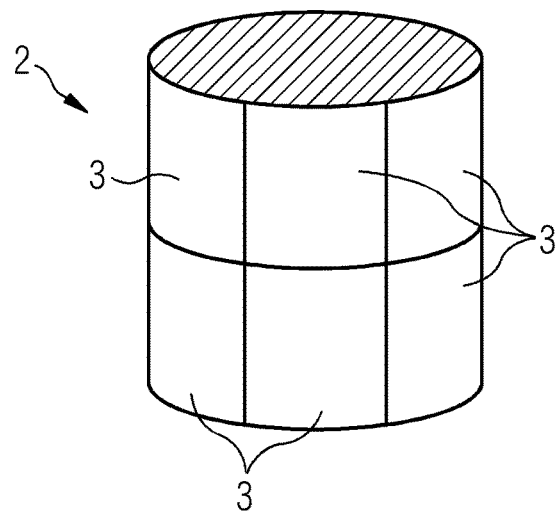
FIG. 2 depicts an example of an optical display apparatus.

FIG. 2 depicts an embodiment of an optical display apparatus 2 in the form of a cylindrical signaling lamp, as may be assembled on a medical device. The view in the direction of travel of the medical device is depicted. The optical display apparatus 2 has two rows of luminous segments 3, which specify the short-term and the medium-term direction of travel, arranged above one another. The two central luminous segments 3 indicate a direction of travel straight ahead, the two left-hand luminous segments 3 indicate a direction of travel to the right and the two right-hand luminous segments 3 indicate a direction of travel to the left (e.g., as seen in the direction of travel of the medical device).

Figure 3:
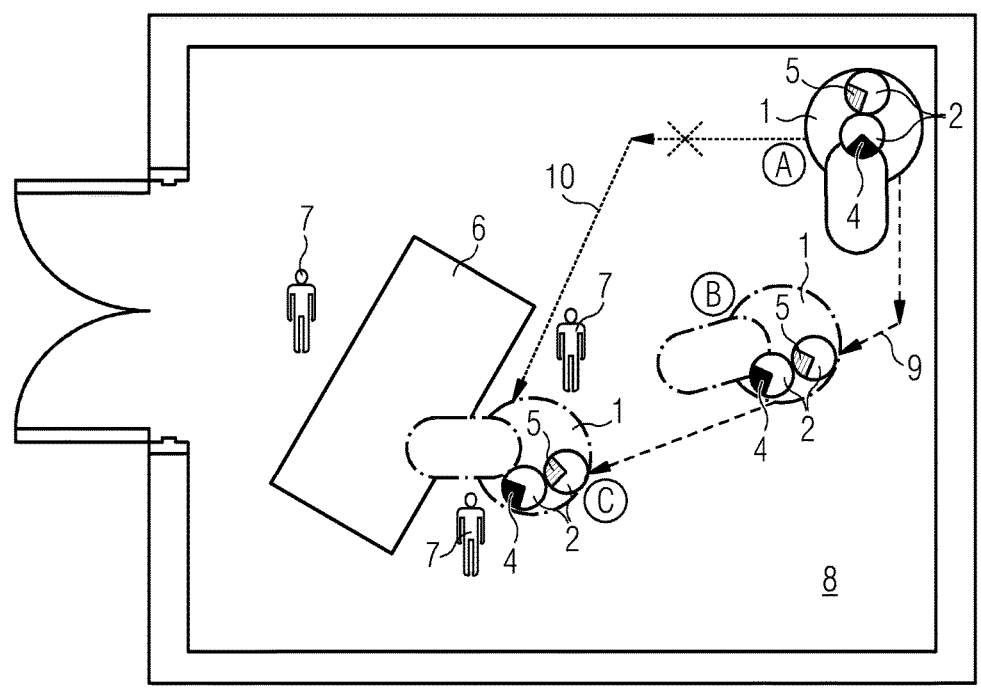
FIG. 3 depicts an example of a visualization of a route in an operating theater.

FIG. 3 depicts, as an example of a medical device drivable by way of a motor, a mobile C-arm x-ray device 1 on wheels that travels autonomously or semi-autonomously on the floor along a planned route 9 in an operating theater 8. The planned route 9 starts at the start position A and leads via the intermediate position B to the target position C at the operating table 6. So that the staff 7 may identify the planned route 9 in advance, the mobile C-arm x-ray device 1 has an optical display apparatus 2 that, by circular segments, indicates a first direction of travel 4, represented by the black circular segment, and a second direction of travel 5, represented by the hatched circular segment.

In the start position A, the short-term first direction of travel 4 points straight ahead, whereas the medium-term second direction of travel 5 points to the left in the direction of travel. In the intermediate position B, the short-term first direction of travel 4 and the medium-term second direction of travel 5 point straight ahead. In the target position C just in front of the operating table 6, the first direction of travel 4 still points straight ahead, whereas the second direction of travel 5 points to the right.

By way of the optical display apparatus 2, the staff 7 may identify in good time the planned route 9 the mobile C-arm x-ray device 1 takes. Of course, the alternative route 10 from the start position A to the operating table 6 may also be possible; however, according to plan, it is not taken by the C-arm x-ray device.

The use includes providing safety for the user and persons in the area since they may better estimate the planned route of the autonomous device. This leads to higher acceptance of the system (e.g., psychological aspects) and to more safety (e.g., additional option of refusing clearance to travel).

Although the invention was, in detail, illustrated and described more closely by the exemplary embodiments, the invention is not restricted by the disclosed examples and other variants may be derived therefrom by a person skilled in the art, without departing from the scope of protection of the invention. In particular, the display apparatus may also be used for patient couches.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A mobile medical device drivable on rollers or wheels on a floor by way of a motor, the mobile medical device configured to take a planned route, the mobile medical device comprising:
    an optical display apparatus configured to optically display a plurality of future movement features of the mobile medical device on the planned route,
    wherein the optical display apparatus comprises a plurality of luminous segments,
    wherein the plurality of future movement features is displayable by a spatial arrangement of the plurality of luminous segments, and
    wherein the optical display apparatus is configured to display a first movement feature of the plurality of future movement features occurring after a first period of time in a first luminous segment of the plurality of luminous segments and a second movement feature of the plurality of future movement features occurring after a second period of time in a second separate luminous segment of the plurality of luminous segments.

2. The mobile medical device of claim 1, wherein each movement feature of the plurality of future movement features is a direction of travel, a driving speed, or both the direction of travel and the driving speed.

3. The mobile medical device of claim 1, wherein the first movement feature and the second movement feature are displayed using different colors.

4. The mobile medical device of claim 3, wherein the first period of time is between one and three seconds and the second period of time is between three and ten seconds.

5. The mobile medical device of claim 1,
    wherein each future movement feature of the plurality of future movement features is a direction of travel.

6. The mobile medical device of claim 5, further comprising:
    a control unit configured to establish the first period of time and the second period of time with aid of a current driving speed of the mobile medical device.

7. The mobile medical device of claim 1, further comprising:
    a control unit configured to establish the first period of time and the second period of time with aid of a current driving speed of the mobile medical device.

8. The mobile medical device of claim 1, wherein the first period of time is between one and three seconds and the second period of time is between three and ten seconds.

9. The mobile medical device of claim 1, wherein the plurality of luminous segments is arranged in a plurality of rows and plurality of columns.

10. The mobile medical device of claim 9, wherein each column of the plurality of columns displays a different direction of travel.

11. The mobile medical device of claim 9, wherein a first row of the plurality of rows is configured to display the first movement feature occurring after the first period of time, and
    wherein a second row of the plurality of rows is configured to display the second movement feature occurring after the second period of time.

12. The mobile medical device of claim 9, wherein each row of the plurality of rows displays a different direction of travel.

13. The mobile medical device of claim 9, wherein a first column of the plurality of columns is configured to display the first movement feature occurring after the first period of time, and
    wherein a second column of the plurality of columns is configured to display the second movement feature occurring after the second period of time.

14. A method for operating a mobile medical device drivable on rollers or wheels on a floor by way of a motor, with planning of a future route, the method comprising:
    providing an optical display apparatus of the mobile medical device, the optical display apparatus having a plurality of luminous segments configured to display a plurality of future movement features of the mobile medical device;
    optically displaying a first movement feature of the plurality of future movement features of the mobile medical device occurring after a first period of time in a first luminous segment of the plurality of luminous segments; and
    optically displaying a second movement feature of the plurality of future movement features of the mobile medical device occurring after a second period of time in a second, separate luminous segment of the plurality of luminous segments.

15. The method of claim 14, wherein each movement feature of the plurality of future movement features is a direction of travel, a driving speed, or both the direction of travel and the driving speed.

16. The method of claim 14, wherein the first movement feature and the second movement feature are displayed using different colors.

17. The method of claim 16, wherein the first period of time is between one and three seconds and the second period of time is between three and ten seconds.

18. The method of claim 14,
    wherein each future movement feature of the plurality of future movement features is a direction of travel.

19. The method of claim 18, further comprising:
    establishing, by a control unit, the first period of time and the second period of time with aid of a current driving speed of the mobile medical device.

20. The method of claim 14, further comprising:
    establishing, by a control unit, the first period of time and the second period of time with aid of a current driving speed of the mobile medical device.

* * * * *